(12) United States Patent
Paraschac

(10) Patent No.: US 6,447,528 B2
(45) Date of Patent: Sep. 10, 2002

(54) MULTIPLE HEADED INSTRUMENT FOR CORNEAL SURGERY

(75) Inventor: Joseph A. Paraschac, Mountain View, CA (US)

(73) Assignee: Addition Technology, Inc., Fremont, CA (US)

( * ) Notice: Subject to any disclaimer, the term of this patent is extended or adjusted under 35 U.S.C. 154(b) by 0 days.

(21) Appl. No.: 09/860,170

(22) Filed: May 17, 2001

Related U.S. Application Data

(60) Provisional application No. 60/205,791, filed on May 17, 2000.

(51) Int. Cl.[7] .............................. A61B 17/00; A61F 9/00
(52) U.S. Cl. ........................................ 606/190; 606/166
(58) Field of Search ................................. 606/190, 166

(56) References Cited

U.S. PATENT DOCUMENTS

| | | | | |
|---|---|---|---|---|
| 3,751,761 A | * | 8/1973 | Weiland | 452/117 |
| 4,579,116 A | * | 4/1986 | Catalano | 600/217 |
| 5,224,950 A | | 7/1993 | Prywes | |
| 5,352,219 A | * | 10/1994 | Reddy | |
| 5,403,335 A | | 4/1995 | Loomas et al. | |
| 5,411,510 A | * | 5/1995 | Fugo | 128/898 |
| 5,653,725 A | * | 8/1997 | Simon et al. | 606/166 |
| 5,713,915 A | * | 2/1998 | Van Heugten et al. | 606/166 |
| 5,824,086 A | | 10/1998 | Silvestrini | |
| 5,843,105 A | | 12/1998 | Mathis et al. | |
| 5,846,256 A | | 12/1998 | Mathis et al. | |
| 6,231,582 B1 | * | 5/2001 | Gandianco et al. | 606/166 |
| 6,251,118 B1 | * | 6/2001 | Proudfoot et al. | 606/166 |

FOREIGN PATENT DOCUMENTS

| | | |
|---|---|---|
| WO | WO 98/03136 | 1/1998 |

\* cited by examiner

*Primary Examiner*—Rodney M. Lindsey
(74) *Attorney, Agent, or Firm*—McCutchen, Doyle, Brown & Enersen

(57) ABSTRACT

The present invention involves a surgical instrument for guiding a delamination instrument into the cornea of a human eye. The instrument generally includes a handle portion and an end portion. The end portion has at least two flat (or substantially flat) members extending therefrom and in different directions. Each of the members being adapted to be inserted through an incision in the cornea to form a guide for a corneal delamination instrument. With at least two members extending in different directions one may easily access either pocket formed from a corneal incision with a single tool.

3 Claims, 5 Drawing Sheets

MULTIPLE HEADED INSTRUMENT FOR CORNEAL SURGERY

CROSS-REFERENCE TO RELATED APPLICATION

This application claims priority under 35 U.S.C. § 119 (e) to U.S. Provisional Application Ser. No. 60/205,791, filed May 17, 2000. The contents of this application is hereby incorporated by reference into the present disclosure.

FILED OF THE INVENTION

The present invention generally relates to the field of eye surgery and more particularly to a method and apparatus for introducing a corneal delaminator into the cornea of an eye.

BACKGROUND OF THE INVENTION

Anomalies in the shape of the cornea of an eye can cause vision disorders such as axial myopia ("nearsightedness") and axial hyperopia ("farsightedness"). In certain cases, the cornea may be reshaped to correct or improve vision. In general, the cornea may be flattened to correct nearsightedness and steepened to correct farsightedness. Various surgical procedures have been used to reshape the cornea and affect vision corrections or improvements. These procedures include placement of implants within the cornea to reshape the cornea. In this procedure an incision is made in the cornea to facilitate forming a channel therefrom for receiving the implant(s). The channel may be formed using, for example, a delaminator as described in U.S. Pat. No. 5,403,335, entitled, *Corneal Vacuum Centering Guide And Dissector*; U.S. Pat. No. 5,843,105, entitled, *System For Inserting Material Into Corneal Stroma*; or U.S. Pat. No. 5,846,256, entitled, *Device And Method For Inserting A Biocompatible Material Into The Corneal Stroma*, all of which are incorporated herein by reference in their entirety. A glide may be inserted through the incision and manipulated into a preformed pocket to serve to guide the dissector into the channel. Various instruments for this purpose are known and are described, for example, in PCT International Publication No. WO 98/03136 of PCT International Application No. PCT/US97/12684 and entitled, *Ophthalmosurgical Instruments And Methods Of Use* (hereinafter "the Instruments Publication"). Since it is generally preferred to minimize the time of any surgery, there remains a need to improve procedure efficiencies.

SUMMARY OF THE INVENTION

The present invention involves a surgical instrument for guiding a delamination instrument into the cornea of a human eye. The instrument generally includes a handle portion and an end portion. The end portion has at least two flat (or substantially flat) members extending therefrom and in different directions. Each of the members being adapted to be inserted through an incision in the cornea to form a guide for a corneal delamination instrument. With at least two members extending in different directions, one may easily access either pocket formed from a corneal incision with a single tool. According to another aspect of the invention, the members form an angle of about 40° to 150° with each other. According to yet another aspect of the invention, the instrument may include a support arm coupling the members to the handle portion, each of the members forming an angle of about 15° to 60° with the support arm.

The above is a brief description of some of the advantages of the invention. Other features, advantages and embodiments of the invention will be apparent to those skilled in the art from the following description, accompanying drawings and appended claims.

DESCRIPTION OF THE DRAWINGS

Like numerals indicate like elements throughout the drawings.

DETAILED DESCRIPTION

Figure 1:
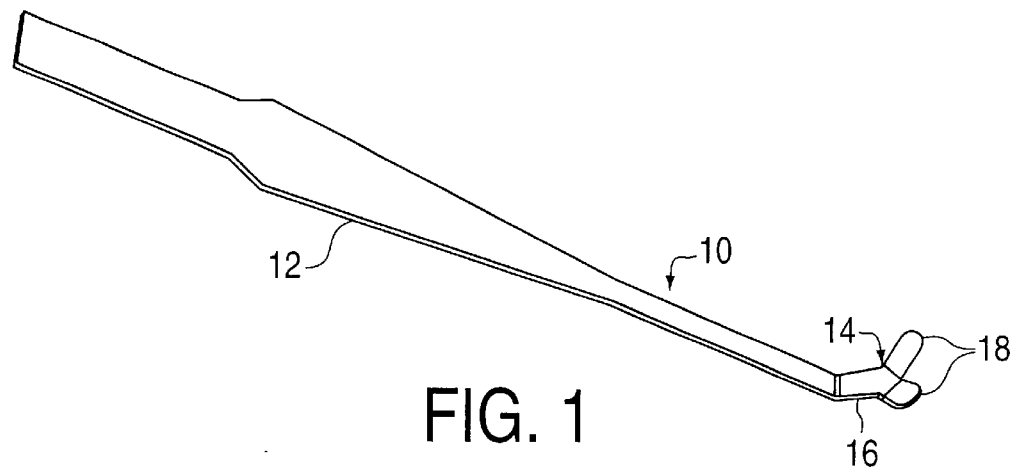
FIG. 1 is a perspective view of a glide constructed in accordance with the principles of the present invention.

Referring to FIG. 1, a surgical instrument constructed in accordance with the principles of the invention and generally indicated with reference numeral 10 is shown. Instrument 10 is a glide for corneal delaminators such as those described in U.S. Pat. Nos. 5,403,335, 5,843,105 and 5,846,256, which are referenced above and are incorporated by reference herein in their entirety. The instrument or glide 10 generally includes a handle portion 12 and an end portion 14. The midsection of the handle portion can be enlarged or configured to give the user a comfortable grip, and to give better control over the instrument. End portion 14 generally includes member or arm 16, which extends from handle portion 12, and heads or prongs 18, which extend from arm 16 and are preferably flat or substantially flat. Although member or arm 16 is shown as a flat member, it may have other configurations.

Figure 2:
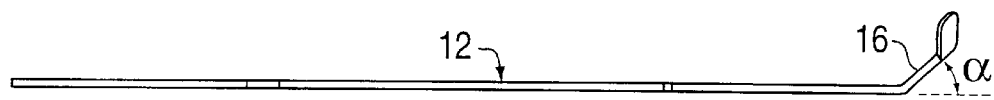
FIG. 2 is a side elevational view of the blade of FIG. 1.
Figure 5:
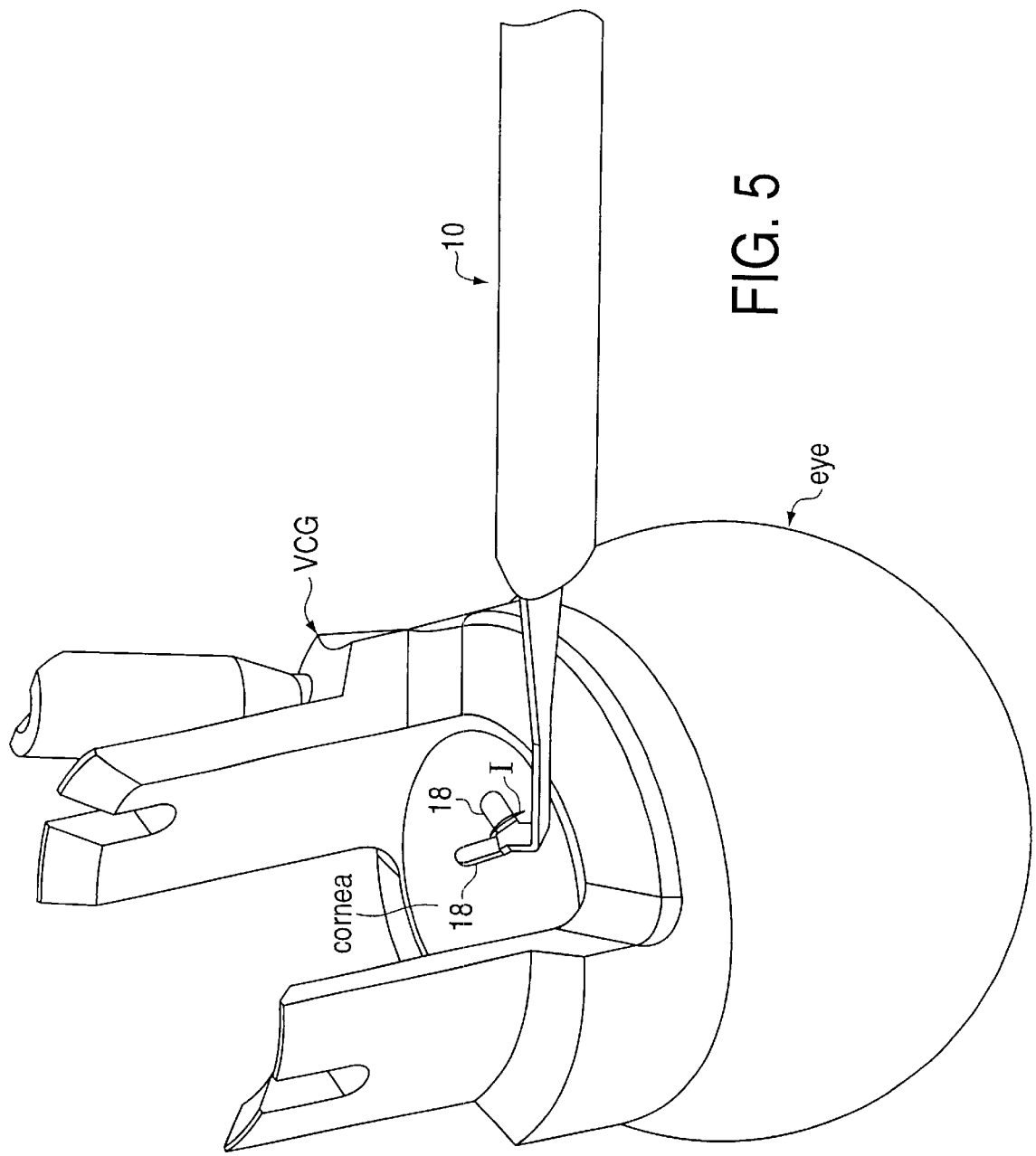
FIGS. 5 and 6 illustrate use of the glide of FIG. 1 to facilitate inserting into a cornea of an eye a delaminator to form clockwise and counterclockwise channels in the cornea.
Figure 6:
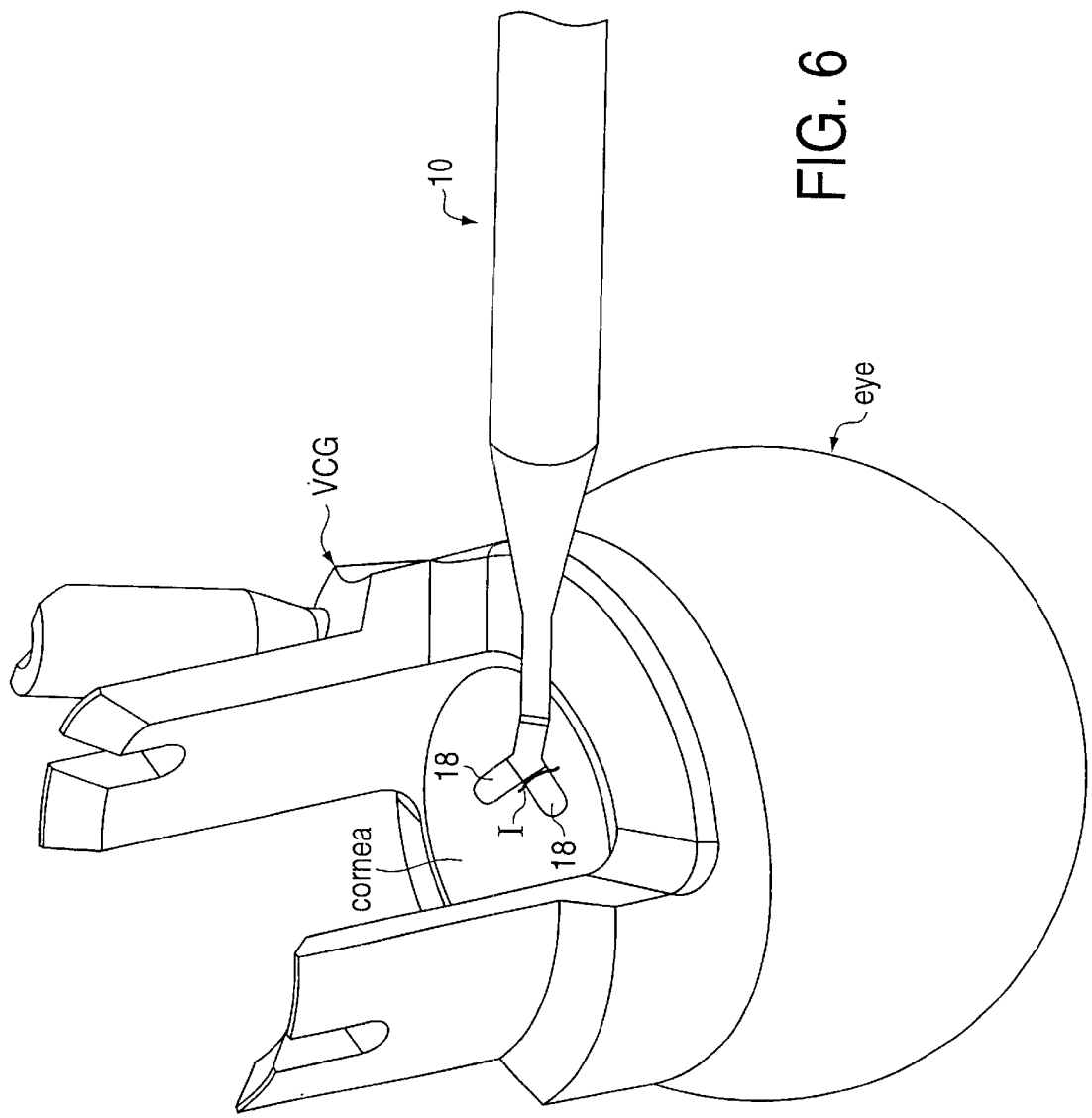

Referring to FIG. 2, further aspects of the invention will be described. Arm 16 and handle portion 12 preferably form a nonzero angle. This angle is generally designated with reference character and preferably is about 20° to 70° and most preferably about 40° to 50°. This angle is designed to allow the handle portion 12 to clear the patient's eyebrow ridge, while the end portion 14 is in position on the cornea as shown in FIGS. 5 and 6. The handle portion and arm also preferably are thick enough to structurally support heads 18 and may have a thickness of about 0.012 inches.

Figure 3:
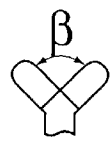
FIG. 3 is an end view of the blade of FIG. 1.

Referring to FIG. 3, multiple heads are shown extending in different directions from arm 16. The heads preferably are angularly spaced from each other by an angle of about 40°–150° and more preferably about 80°±10°. This angle may be measured from the inner edges of the heads as shown or from their centroidal axes. Heads 18 preferably have a thickness of about 0.005 inches ±0.001 inches, and are shown with a rounded or blunt end. The blunt ends make the ends or tips easier to insert into the preformed corneal pockets, and minimize trauma to the surrounding tissue. It should be understood that other shapes, sharp ends (for example, to assist in forming a pocket if desired) or any combination thereof may be used without departing from the scope of the invention.

Figure 4:
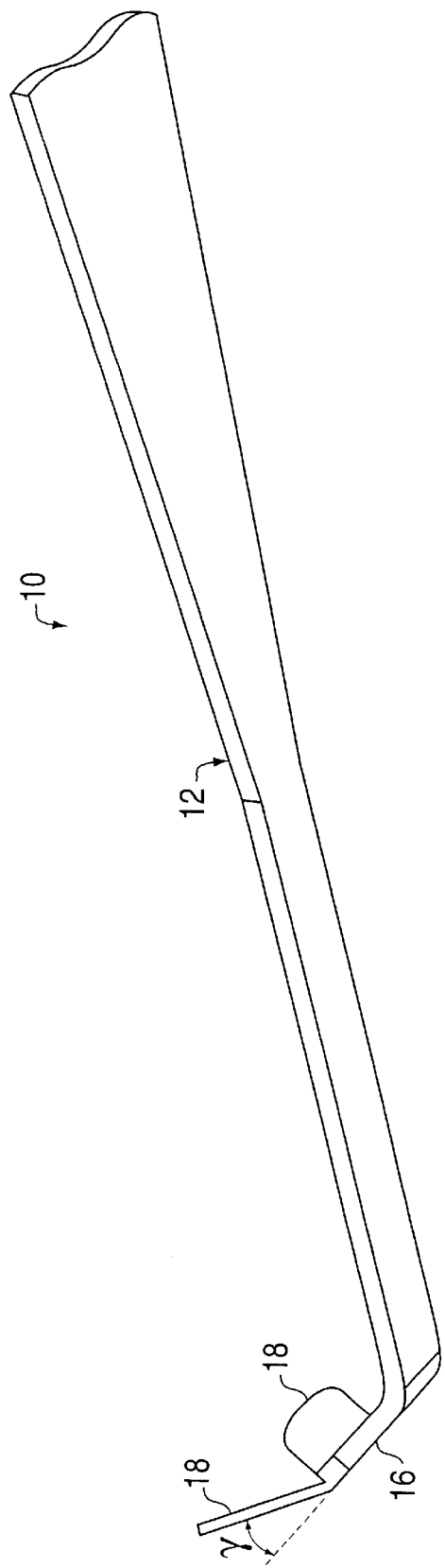
FIG. 4 is a further view showing yet a further aspect of the blade of FIG. 1 (the angle γ not shown in FIGS. 1 and 2).

Referring to FIG. 4, heads 18 preferably form at an angle of about 15°–60° with arm 16, and more preferably about 25° to 35°. This angle is generally designated with reference character y and serves to maintain the surgeon's hand in nearly the same position, whether the glide is being used in the clockwise pocket as shown in FIG. 5, or the clockwise pocket as shown in FIG. 6. In addition, the angle serves to provide an angled lead or shoe horn for the channel forming delamination instrument. The delaminator blade of the delamination instrument is inserted beneath respective head 18.

The instrument may be made of stainless steel, titanium, or other biocompatible structural material. As shown, it can be designed to be manufactured with sheet metal forming processes including photochemical etching, stamping, coining, and forming. The flat part manufactured according to these methods may be attached to an ergonomically correct handle, making a two piece assembly. It is possible to alter the design slightly to make it easily manufacturable by such machining processes as grinding and milling, so that an attractive and useful handle would be machined from the same piece of raw material, making a single piece glide.

Figure 7:
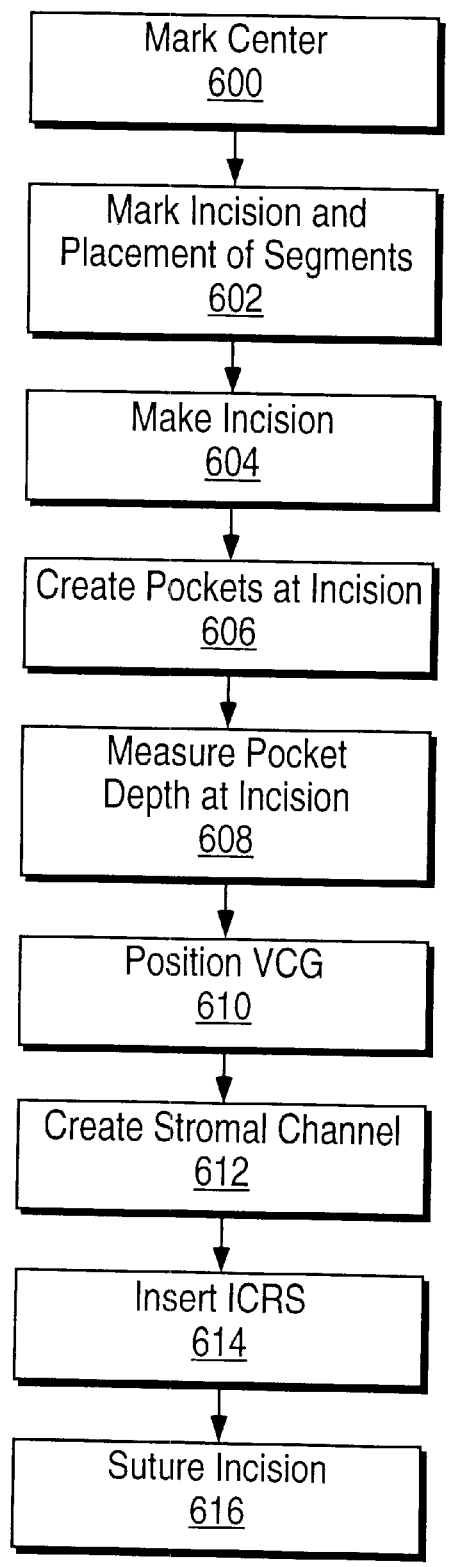
FIG. 7 is a flow chart diagrammatically diagramming steps for a procedure.

The instrument 10 may be used to guide/introduce a channel forming delaminator (such as any of the delaminators described in the Instruments Publication) into the cornea of a human eye. FIG. 7 shows a flow chart describing a method of placing an implant in a cornea using the multiple headed instrument of the present invention and instruments described in the Instruments Publication. At step (600) the geometric center of the cornea is marked with a blunt instrument (e.g., a Sinskey Hook) using an operating microscope for fixation and an 11-mm zone marker can be used to aid in locating the center point. A sterile marking pen may be used to enhance the mark. This center mark is used as the reference point throughout the surgical procedure. The specific surgical technique described herein is for purposes of example only, and may be slightly altered to provide the surgeon with flexibility during the corneal implant surgical procedure. Surgical instruments that can be used during the procedure are illustrated in FIG. 1 of PCT International Publication No. WO 98/03136, and the Instruments Publication (referenced above). Prior to the use in the procedure, all surgical instruments in the sterile field are to be rinsed with sterile water and wiped using a lint-free instrument wipe.

At step (602), the contact surface (e.g., surface 102 in the Instruments Publication) of the incision and a placement marker (e.g., marker 100 in the Instruments Publication) is marked, using a sterile marking pen, for example. Other non-toxic, biocompatible dyes which do not run may be alternatively used. The incision and placement marker (100) is next centered on the center mark created at the geometric center described above, by lining up, for example, the reticle 106 (as shown in the Instruments Publication) with the center mark. The contact surface (102), including, for example, surfaces (103), (104) and (105) (as shown in the Instruments Publication) are contacted lightly against the cornea, making an inked marking where the radial incision will be made and where the corneal implants such as corneal ring segments (as described in U.S. Pat. No. 5,824,086, which is incorporated herein by reference in its entirety) or other material will be positioned. A visual verification is made that the marks (103) are at least 1 mm from the limbus in all directions. If the marks (e.g., 122 as shown in the Instruments Publication) are too close to the limbus, re-marking of the geometric center of the cornea is required to get closer to the actual geometric center.

A pachymetry measurement is made to determine the thickness of the corneal tissue at the incision site. Next, a calibrated, diamond knife is set to about 0.430 mm (about 430 μm). Alternatively, it can be set at about 68% of the intraoperative pachymetry reading taken at the incision site. The diamond should either have an angled cutting edge of 15° or less, or have a rectangular blade of 1 mm width or less. Preferably, a recording of the integrity of the diamond blade tip and the inspection of the dissectors is made on a surgical video, although this is not essential to the inventive method. The actual knife setting is recorded on the surgical video for record keeping purposes.

At step (604), a radial incision is made by tracing to the outside edge of the incision mark, see FIG. 10 in the Instruments Publication. The incision length may range from about 1.0 to 1.8 mm, and is preferably about 1.3 mm. Special care should be taken to ensure that the incision is kept approximately 1 mm away from the limbus. The incision area is then thoroughly irrigated with balanced salt solution after completing the incision. A Merocel® spear or equivalent is used to remove any loose epithelial cells and excess balanced salt solution from the edges of the incision. The epithelium may be rolled away from the incision edges.

The incision is again thoroughly irrigated with balanced salt solution prior to any instrument insertion. It is recommended that the surgeon increase the magnification of the microscope to enhance visualization during the next step. At step 606, an instrument with a spreader tip, such as shown with reference numeral 156 in the Instruments Publication, is inserted vertically down into the incision until it contacts the bottom of the incision. A blunt dissection or pocket is then created on one side of the base of the incision by carefully rotating the blade or spreader tip of the instrument, preferably within a single stromal plane. The procedure is then repeated on the other side of the incision base. The resultant pockets should be at the same depth as the incision base, as wide as the full incision length, and extend to the full length of the spreader tip (156).

The corneal thickness gauges 250 as in the Instruments Publication, and may be used to estimate the depth for both pockets at step (608). If the pockets are not deep enough in the corneal stroma, make the incision slightly deeper with the diamond knife and create a second pocket at a deeper level with the spreader (150). Alternatively, a depth measuring system as described in copending U.S. Provisional Patent Application No. 60/140,397, filed on Jun. 21, 1999 and entitled, *Corneal Depth Measuring System And Method* (Attorney Docket No. 25169-30058.00) can be used. Alternatively, an apparatus for determining the depth of an incision or pocket in tissue, such as corneal tissue, utilizing a differential variable reluctance transducer (DVRT) may be used.

Such a pocket may be made by making an incision (e.g., a controlled-depth incision) into the tissue of a patient and delaminating the tissue at the bottom of the incision to create a tissue pocket. The tissue has an anterior surface. It may be the corneal tissue of an eye where the anterior surface of the corneal tissue is the anterior surface. A reference base component of a depth measuring apparatus is inserted into a tissue pocket. A movable measurement component is placed in contact with the anterior surface of the tissue (e.g., the anterior surface of a cornea) such that the distance between the reference base component and the movable measurement component represents the depth of the pocket (e.g., a corneal pocket).

In one embodiment, the reference base component and the movable measurement component are integrated into a single-piece depth measurement gauge. The single-piece depth measurement gauge generally comprises a housing having a base configured for insertion into corneal tissue, a member coupled and movable relative to the housing and configured to rest one end on an anterior surface of the corneal tissue, and a sensing and reference coil. The sensing coil is disposed within the housing and electrically coupled to a first current source. The sensing coil is adapted to interact with the movable member to vary a measurable parameter, such as reluctance, of the sensing coil, depending upon the position of the interacting member. The reference coil is also disposed within the housing and is electrically coupled to a second current source. By comparing the reluctance of each coil, the effects, which are independent of the position of the interacting member, can be corrected.

The electrical circuit may include a temperature gradient compensating circuit to remove the effects of a temperature gradient between the sensing and reference coils.

Returning to FIG. 7, at step (610) the incision and placement marker (100) is indexed into the vacuum centering guide (VCG), as described in the Instruments Publication, and the reticle (106) is aligned with the center mark to center the VCG on the center mark. The VCG is then lowered to contact the sclera of the eye while maintaining centration, and vacuum is slowly applied. As noted in the description above, proper placement of the VCG over the incision and placement marker (100), together with proper alignment of the marker (100) on both the center mark and the actual incision, ensure that a window in the VCG is centered on the incision site. The vacuum should start in the range of 12–15 inches of Hg. Once a vacuum seal has been established, a confirmation that the VCG is properly placed is made by checking centration. If the VCG is not properly positioned, the vacuum must be released, and step (610), as described above, must be repeated. If the VCG is determined to be properly positioned, the vacuum is then slowly increased to 18–20 inches of Hg. It is recommended that the vacuum not exceed 22 inches of Hg. The incision and placement marker (100) is then removed from the VCG.

Every effort should be made to complete the channel dissection and to remove the VCG as quickly as possible in order to minimize the vacuum time. It is recommended that the vacuum time not exceed five minutes. While maintaining the position of the VCG, a counterclockwise (CCW) dissector (300) (see the Instruments Publication), is inserted into the VCG at step (612). The dissector body (300) should be rotated until the tip of the dissector blade (310, see the Instruments Publication) is adjacent to the incision site.

One head of glide is inserted in the incision "I" as shown in FIG. 5 above, at least 1 mm into the counterclockwise pocket and the dissector tip of the blade, such as shown for example in the Instruments Publication, is rotated under the head 18 of the glide. Counterclockwise rotation of the dissector body (300) (see the Instruments Publication) allows the dissector tip to enter the pocket underneath the glide 10. The dissector blade (310) is then advanced approximately 1 mm to 2 mm, then stopped. The glide 10 is removed while leaving the dissector tip in position in the pocket.

While holding the VCG vertically with one hand, the operator rotates the dissector (330) counterclockwise to create a stromal channel. Rotation of the dissector (330) in a counterclockwise direction is continued until the support spoke (310) of the dissector blade (310) contacts the incision edge. Then the dissector blade (310) is removed from the channel by rotating the dissector body (330) clockwise until the dissector tip exits the channel, and the dissector (330) is then removed from the VCG.

While maintaining the position of the VCG, the clockwise (CW) dissector (330) may be inserted into the VCG. The dissector body (330) is rotated until the tip of the dissector is adjacent to the incision site. Next, multiple head glide 10 is inserted at least 1 mm into the opposite pocket as shown in FIG. 6 and the dissector tip is rotated under the head 18 of the glide 10. Clockwise rotation of the dissector body (330) drives the dissector tip into the pocket. The dissector tip should be inserted underneath the glide head 18 to enter the pocket. The dissector tip (310) is next advanced approximately 1 mm to 2 mm, then stopped in its position. The glide 18 is removed while leaving the dissector tip in position in the pocket.

While holding the VCG vertically with one hand and with further reference to the Instruments Publication, the operator rotates the dissector (330) clockwise from the incision to create a second stromal channel. The clockwise rotation of the dissector (330) is continued until the support spoke (310) of the dissector blade (310) contacts the incision edge. Then the dissector blade (310) is removed from the channel by rotating the dissector body (330) counterclockwise until the dissector tip exits the channel. The dissector (330) is then removed from the VCG.

The vacuum is next released and the VCG is removed from the eye. Any stromal debris from the incision site is removed and the incision area is again thoroughly irrigated, using balanced salt solution, prior to insertion of each segment into the stromal channel. Optionally, a small amount of Celluvisc® or an equivalent lubricating agent may be applied to the surface of the cornea to avoid direct contact of the segments with the epithelium, although this is not preferred.

Each corneal implant, such as the cornea segment described above, is picked up using forceps (500) as described above. The leading end of each segment is fed into the stromal channel from the incision at step (612). One segment is rotated clockwise and the second segment is rotated counterclockwise. The segments have an anterior/posterior orientation. The segment may be placed in the stroma concave side down, such that the cone angle of the segment is most closely matched with the curvature of the cornea. Of course, other biocompatible material, such as a biocompatible gel, may be used as an implant.

Using forceps (500) or a Sinskey Hook, the segments are manipulated into the desired location within the channel, aligning the outside edge of the segments with the ink markings (123), and the leading ends of the segments with ink markings (125) created by the incision and placement marker at Step (602).

Again any stromal debris is removed from the incision area, and the incision area is thoroughly irrigated with balanced salt solution. The tissue edges of the incision are gently approximated to close at step (616), and the incision may be closed with one to two interrupted sutures using an ophthalmic suture, preferably 10-0 or 11-0 nylon or equivalent. The suture depth should be to the level of the stromal pocket. Care should be taken to avoid microperforation by the suture needle. If two sutures are placed, the sutures should trisect the incision line from the superior and inferior aspects of the incision to insure apposition of the anterior edges of the incision. The anterior incision edges preferably are opposed to prevent epithelial cells from entering the incision Other modifications to the embodiments described above will be apparent to those skilled in the art. The disclosures of all prior art references described above are incorporated herein by reference. For example, the dimensions in the drawings are merely provided for example.

What is claimed is:

1. A surgical instrument for forming a pocket in the cornea of a human eye, the instrument comprising a handle portion and an end portion, said end portion having at least two substantially flat members extending therefrom and in different directions, each of said flat members being adapted to be inserted through an incision in the cornea to form a guide for a corneal delamination instrument.

2. The instrument of claim 1 wherein said flat members form an angle of about 40° to 150° with each other.

3. The instrument of claim 1 further including a support arm coupling said substantially flat members to said handle portion, each of said substantially flat members forming an angle of about 15° to 60° with said support arm.

* * * * *